US006802968B2

(12) United States Patent
Leavesley et al.

(10) Patent No.: US 6,802,968 B2
(45) Date of Patent: Oct. 12, 2004

(54) CHROMATOGRAPHY APPARATUS

(75) Inventors: Peter J. Leavesley, Charlottesville, VA (US); Peter C. Van Davelaar, Charlottesville, VA (US); Robert D. Lockman, Northville, MI (US); Ivan Hargro, Plainfield, NJ (US); Jeffrey A. Horsman, Charlottesville, VA (US); Peter C. Rahn, Palmyra, VA (US)

(73) Assignee: Biotage, Inc., Charlottesville, VA (US)

( * ) Notice: Subject to any disclaimer, the term of this patent is extended or adjusted under 35 U.S.C. 154(b) by 92 days.

(21) Appl. No.: 10/172,466

(22) Filed: Jun. 14, 2002

(65) Prior Publication Data

US 2002/0153294 A1 Oct. 24, 2002

Related U.S. Application Data

(63) Continuation of application No. 09/687,801, filed on Oct. 13, 2000, now Pat. No. 6,436,284, which is a continuation-in-part of application No. 09/548,261, filed on Apr. 12, 2000, now Pat. No. 6,294,087, which is a continuation-in-part of application No. 09/548,214, filed on Apr. 12, 2000, now Pat. No. 6,221,252, which is a continuation-in-part of application No. 09/137,019, filed on Aug. 20, 1998, now Pat. No. 6,132,605, which is a division of application No. 09/137,278, filed on Aug. 20, 1998, now Pat. No. 6,139,733, which is a continuation-in-part of application No. 08/968,287, filed on Nov. 12, 1997, now Pat. No. 6,068,766.

(51) Int. Cl.[7] ............................................. B01D 15/08
(52) U.S. Cl. ...................... 210/198.2; 210/656; 96/101
(58) Field of Search ............................... 210/635, 656, 210/659, 198.2, 232, 238, 282; 96/101, 105, 106

(56) References Cited

U.S. PATENT DOCUMENTS

| 1,808,441 | A | 6/1931 | Hinkston | 101/163 |
|---|---|---|---|---|
| 3,266,554 | A | 8/1966 | Brownrigg | 159/5 |
| 3,398,512 | A | 8/1968 | Perkins, Jr. et al. | 55/386 |
| 3,440,864 | A | 4/1969 | Blume | 73/61.53 |
| 3,483,986 | A | 12/1969 | Wright | 210/198.2 |
| 3,615,235 | A | 10/1971 | Hrdina | 210/198.2 |
| 3,682,315 | A | 8/1972 | Haller | 210/233 |
| 3,692,669 | A | 9/1972 | Bauman | 210/31 |
| 3,704,729 | A | 12/1972 | Tomlinson | 138/90 |
| 3,763,879 | A | 10/1973 | Jaworek | 137/268 |
| 3,902,849 | A | 9/1975 | Barak et al. | 210/198.2 |
| 3,978,575 | A | 9/1976 | Beyer et al. | 29/426.4 |
| 4,093,550 | A | 6/1978 | Stahl et al. | 210/198.2 |
| 4,163,462 | A | 8/1979 | Milo | 138/90 |
| 4,250,035 | A | 2/1981 | McDonald et al. | 210/198.2 |
| 4,283,280 | A | 8/1981 | Brownlee | 210/198.2 |
| 4,286,139 | A | 8/1981 | Taylor | 219/208 |
| 4,452,070 | A | 6/1984 | Kipp | 73/49.8 |
| 4,457,846 | A | 7/1984 | Munk | 210/656 |
| 4,483,374 | A | 11/1984 | Siemion | 210/656 |
| 4,529,007 | A | 7/1985 | Goforth | 138/89 |

(List continued on next page.)

OTHER PUBLICATIONS

Larry Miller, et al., "Solid injection, a new technique for application of insoluble samples in preparative liquid chromatography," Journal Of Chromatography, vol. 484 (1989), pp. 259–265.

J. Kriz et al., "Solid sample introduction in preparative high–performance liquid chromatography: separation of diamantanols," Journal Of Chromatography, vol. 248 (1982), pp. 303–307.

(List continued on next page.)

Primary Examiner—Ernest G. Therkorn
(74) Attorney, Agent, or Firm—Fish & Richardson P.C.

(57) ABSTRACT

An apparatus for use in liquid chromatography involves a column filled with media bounded axially by first and second porous plates. The column has an inlet end with an inflow region between the inlet end and the first porous plate. The column also has an outlet end with an outflow region between the outlet end and the second porous plate. The inflow region may be substantially longer than the outflow region. The porous plates may be moveable under pressure so as to compress the media.

34 Claims, 9 Drawing Sheets

U.S. PATENT DOCUMENTS

| | | | |
|---|---|---|---|
| 4,551,249 A | 11/1985 | Shackelford et al. | 210/198.2 |
| 4,565,632 A | 1/1986 | Hatch et al. | 210/656 |
| 4,587,014 A | 5/1986 | America | 210/198.2 |
| 4,597,866 A | 7/1986 | Couillard | 210/198.2 |
| 4,625,765 A | 12/1986 | O'Donnell et al. | 138/89 |
| 4,636,316 A | 1/1987 | Harris et al. | 210/656 |
| 4,655,917 A | 4/1987 | Shackelford et al. | 210/198.2 |
| 4,670,141 A | 6/1987 | Shackelford et al. | 210/198.2 |
| 4,719,011 A | 1/1988 | Shalon et al. | 210/198.2 |
| 4,732,687 A | 3/1988 | Muller et al. | 210/656 |
| 4,737,284 A | 4/1988 | Hauke | 210/198.2 |
| 4,737,292 A | 4/1988 | Ritacco et al. | 210/656 |
| 4,797,209 A | 1/1989 | Jackson | 210/656 |
| 4,861,473 A | 8/1989 | Shackelford et al. | 210/198.2 |
| 4,876,005 A | 10/1989 | America | 210/198.2 |
| 4,888,112 A | 12/1989 | Kronwald | 210/198.2 |
| 4,891,133 A | 1/1990 | Colvin, Jr. | 210/198.2 |
| 4,903,941 A | 2/1990 | Nuytten | 251/148 |
| 4,968,421 A | 11/1990 | Spacek et al. | 210/198.2 |
| 4,997,465 A | 3/1991 | Stanford | 55/179 |
| 5,137,628 A | 8/1992 | Hart et al. | 210/198.2 |
| 5,141,635 A | 8/1992 | LePlang | 210/198.2 |
| 5,167,809 A | 12/1992 | Mann et al. | 210/198.2 |
| 5,169,522 A | 12/1992 | Shalon et al. | 210/198.2 |
| 5,188,730 A | 2/1993 | Kronwald | 210/198.2 |
| 5,194,225 A | 3/1993 | Muller et al. | 210/198.2 |
| 5,227,059 A | 7/1993 | Shepherd | 210/198.2 |
| 5,234,599 A | 8/1993 | Cortes et al. | 210/198.2 |
| 5,238,556 A | 8/1993 | Shirkhan | 210/198 |
| 5,324,426 A | 6/1994 | Joseph et al. | 210/198.2 |
| 5,324,427 A | 6/1994 | Traveset-Masanes et al. | 210/198.2 |
| 5,338,448 A | 8/1994 | Gjerde | 210/198.2 |
| 5,366,621 A | 11/1994 | Bidell et al. | 210/198.2 |
| 5,423,982 A | 6/1995 | Jungbauer | 210/198.2 |
| 5,462,660 A | 10/1995 | Singleton | 210/198.2 |
| 5,470,479 A | 11/1995 | Snyder et al. | 210/635 |
| 5,601,708 A | 2/1997 | Leavesley | 210/198.2 |
| 5,614,089 A | 3/1997 | Allington | 210/198.2 |
| 5,670,048 A | 9/1997 | Davison et al. | 210/634 |
| 5,693,223 A | 12/1997 | Yamada et al. | 210/198.2 |
| 6,116,573 A | 9/2000 | Cornette et al. | 251/214 |
| 6,162,362 A | 12/2000 | Ma et al. | 210/656 |
| 6,294,087 B1 * | 9/2001 | Hargro et al. | 210/198.2 |
| 6,436,284 B1 * | 8/2002 | Leavesley et al. | 210/198.2 |
| 6,565,745 B2 | 5/2003 | Hodgin et al. | 210/198.2 |

OTHER PUBLICATIONS

Patrick D. McDonald et al., "Strategies for successful preparative liquid chromatography," Chapter 1. Section 1.6.2.2.6, "Sample Solubility," pp. 79–80, in Brian A. Bidlingmeyer, ed., Preparative Liquid Chromatography, (Amsterdam: Elsevier, 1987).

"Flash Sample Injection Module™," Biotage, a Division of Dyax Corp., (1996).

Snyder, "Introduction To Modern Liquid Chromatograpy, "(New York; John Wiley & Sons, 1979), pp. 228–229, 251, 543, and 635.

Pharmacia K 50 Column, p. 3, Pharmacia Laboratory Columns, XK Column System, pp. 424–426. (cited by Examiner, no copy of).

* cited by examiner

CHROMATOGRAPHY APPARATUS

The present Application is a continuation of U.S. patent Ser. No. 09/687,801, filed on Oct. 13, 2000 now U.S. Pat. No. 6,436,284. U.S. patent Ser. No. 09/687,801 is a continuation-in-part of U.S. patent Ser. No. 09/137,019 filed Aug. 20, 1998, now U.S. Pat. No. 6,132,605 (which is a continuation-in-part of U.S. patent Ser. No. 08/968,287 filed Nov. 12, 1997, now U.S. Pat. No. 6,086,766) and a continuation-in-part of U.S. patent Ser. No. 09/548,261 filed Apr. 12, 2000, now U.S. Pat. No. 6,294,087 (which is a divisional application of U.S. patent Ser. No. 09/137,278 filed Aug. 20, 1998, now U.S. Pat. No. 6,139,733) and a continuation-in-part of U.S. patent Ser. No. 09/548,214 filed Apr. 12, 2000, now U.S. Pat. No. 6,221,252 (which is a divisional application of U.S. patent Ser. No. 09/137,278 filed Aug. 20, 1998, now U.S. Pat. No. 6,139,733).

BACKGROUND OF THE INVENTION

In one aspect, the invention relates to columns used in liquid chromatography. In another aspect, the invention relates to introducing a sample into a chromatography column. The invention, in yet another aspect, relates to an apparatus and method for sealing the openings of vessels; in particular, the apparatus relates to sealing the openings of liquid chromatography cartridges.

Liquid chromatography is a technique for separating the individual compounds that exist in a subject sample. In employing the technique, the subject sample is carried in a liquid, called a mobile phase. The mobile phase carrying the subject sample is caused to migrate through a media, called a stationary phase. Different compounds will have differing rates of migration through the media, which effects the separation of the components in the subject sample. Liquid chromatography is commonly performed with reusable columns or with disposable cartridges, both of which are usually cylindrical, in which the media bed is bounded axially by porous plates, or plates containing defined flow paths, through which the mobile phase will flow. (See U.S. Pat. No. 4,250,035 to McDonald et al.)

Chromatography systems demand that a reliable seal be created between the column and the head through which the mobile phase enters. This is a particular problem in chromatography systems that employ disposable cartridges in which precise tolerances and careful machining that are customarily required for the creation of effective seals will increase manufacturing costs. Methods of sealing liquid chromatography cartridges typically require forcing a sealing head onto or into the cartridge. Some prior art techniques involve forcing a one-piece sealing head with an elastomeric o-ring, connected radially or to an end of the sealing head, into the cartridge. Alternately, a tapered sealing head can be forced into a cartridge without employing an o-ring to create a seal. Other prior art techniques employ o-rings or knife-edges (see U.S. Pat. No. 5,601,708 to Leavesley) oriented axially on a sealing head that create seals with the edges of the cartridges at their open ends.

Chromatography columns and cartridges also demand a close contact between the sealing heads and the media bed. Prior art sealing techniques often create gaps between the sealing head and the media bed. Even small gaps can reduce the resolution of distinct components that can be achieved. At the entrance of a column or cartridge, gaps between the sealing head and the porous plate or media will allow the subject sample to disperse and become diluted. At the exit of a column or cartridge, gaps will create a volume in which distinct fractions of the subject sample, which were separated during migration through the media, can blend back together. Thus, gaps at either end of the media bed can degrade the analytic performance of chromatography columns or cartridges.

When chemists optimize liquid chromatographic separations conditions, they may need to dissolve the sample mixture in a dissolution solvent which may be nonideal for elution. This can result in poor separation and poor recovery of desired components.

One solution to this problem is to pre-absorb the sample onto a media prior to chromatography. This involves dissolving the sample mixture in a suitable solvent and adding an amount of a dry media (usually similar to the media being used for the separation) to this solution. The dissolution solvent is then evaporated off, usually using a rotary evaporator, leaving the sample mixture dry, and absorbed to the media. The pre-absorbed media is then placed at the head of a pre-packed glass, metal or plastic chromatography column, and the optimized chromatographic solvent would flow through the pre-absorbed media and then through the column of separation media. This method has the potential hazard of the operator coming into contact with the dry powdery media both before and after the addition of the sample. This method also can lead to poor separations and recovery.

SUMMARY OF THE INVENTION

In one aspect, the invention in general relates to sealing a chromatography cartridge containing a media bed that forms a stop. The apparatus involves a sealing head that includes a first head piece, a second head piece, and an elastomeric sealing member. The first head piece includes a first compression face and a contact face adapted to contact said stop. The second head piece includes a second compression face and a compression force receiving member. The elastomeric sealing member is at least partially situated between the first and second compression faces. The first head piece, the second head piece, and the elastomeric sealing member are sized to slide easily into a chromatography cartridge having interior walls and containing a chromatography media bed that is bounded axially by porous plates.

In operation, the sealing head is inserted into the cartridge. Friction between the elastomeric sealing member and the cartridge is minimized when the elastomeric sealing member is in an uncompressed state during insertion. After the head has been inserted into the cartridge, the elastomeric sealing member is compressed between the first and second compression faces, by moving the second head piece toward the media bed so that the contact face presses against the stop. Compression of the elastomeric sealing member causes the elastomeric sealing member to expand laterally so that it presses against the interior walls of the cartridge and creates a seal.

The sealing apparatus may be removed from the cartridge by raising the second head piece relative to the first head piece, thus reducing the compression forces on the elastomeric sealing member and lessening its lateral expansion. This reduces the frictional contact between the elastomeric sealing member and the interior walls of the cartridge, so that the sealing member and the first and second head pieces may be more easily removed.

By providing a second sealing apparatus, it is possible to seal both ends of a chromatography cartridge in the manner described above.

In the preferred embodiments, the first head piece contains a body portion and an outwardly-extending shoulder.

The first compression face is located on the shoulder. Additionally, the first and second head pieces are shaped and sized so that the second head piece may slidably receive the body of the first head piece. The first head piece defines a flow path for the passage of a fluid, such as a mobile phase for chromatography. The contact face on the first head piece includes a slight conical concavity that helps to distribute a mobile phase uniformly to the media bed.

In operating the preferred embodiments, the contact face of the first head piece presses against the porous plate while the elastomeric sealing member is compressed axially. This axial compression causes the elastomeric sealing member to expand laterally, thus forming a seal with the interior walls cartridge.

In another aspect, the invention in general relates to sealing chromatography columns containing a first media bed, by creating a plurality of seals. The apparatus involves a sealing head that includes a first head piece, a second head piece, an intermediate head piece, and a plurality of elastomeric sealing members. The first head piece has a body portion and a shoulder that extends farther radially than the body portion. The second head piece and the intermediate head piece define central openings through which the body portion of the first head piece is slidably fitted. The elastomeric sealing members are annular and they circumscribe the body portion of the first head piece. A first elastomeric sealing member is between the shoulder and the intermediate head piece. A second elastomeric sealing member is between the second head piece and the intermediate head piece.

The first and second head pieces, the intermediate head piece, and the elastomeric sealing members are sized to slide easily into the chromatography column.

In operation, the apparatus is inserted into the column. Friction between the elastomeric sealing members and the column is minimized when the elastomeric sealing members are in an uncompressed state during insertion. After the head has been inserted into the column, the elastomeric sealing members are compressed, by moving the first and second head pieces relative to each other, so that the second head piece moves toward the shoulder of the first head piece. The first elastomeric sealing member is compressed between the shoulder and the intermediate head piece. The second elastomeric sealing member is compressed between the intermediate head piece and the second head piece. Compression of the elastomeric sealing members causes them to expand laterally so that they press against the interior walls of the column and create seals.

In alternate preferred embodiments, an inner cartridge fits into an open end of the column. Preferably, the inner cartridge is a sample module. The sample module contains a subject sample. The sample module may also contain chromatography solvents and a chromatography media of either the same or different composition that is used in the column. The shoulder of the first head piece and the first elastomeric sealing member are sized to fit slidably into the sample module, when the first elastomeric sealing member is uncompressed. When a compressive force is applied to the sealing head, the first elastic sealing member forms a seal with the sample module and the second elastic sealing member forms a seal with the column.

Embodiments of these aspects of the invention may include one or more of the following advantages. Insertion of the sealing apparatus into a chromatography cartridge creates minimal friction between the sealing head and the interior walls of the cartridge. Use of the sealing apparatus does not require close tolerances that create a precise fit between the sealing head and the cartridge. A small amount of force is required to create a seal with chromatography cartridges, relative to prior art methods. The sealing apparatus can be easily removed from a chromatography cartridge, so that the cartridge can be replaced. Because use of the apparatus can minimize frictional shear forces during insertion into a chromatography cartridge, wear on elastomeric sealing members is reduced. Using the apparatus can create a high quality seal. Using the apparatus can minimize the gap that is created between a sealing head and the media bed or porous plate, when sealing a chromatography cartridge. Using the apparatus can axially compress the media bed while sealing a chromatography cartridge. The apparatus has the ability to create a seal by the relative motion of two pieces that compress an elastomeric sealing member without exerting axial force on the media itself. The apparatus can also create a seal by pressing the sealing head against a rigid stop within the column. The apparatus can be adapted for sealing chromatography cartridges having media beds of varying lengths and distances from the opening of the cartridge. The invention may be used with any type of column, including disposable pre-packed cartridges, columns with flexible walls, and columns made of, e.g., glass, steel, or a synthetic material. By employing a sample module that is fitted and sealed within the column a subject sample may be analyzed with two different media in one column. The sample module and the column may employ either porous plates or plates having drilled channels to bound the media beds. The outwardly extending shoulder may have any shape that allows it to exert a compressive force on an elastomeric sealing member.

In an alternative aspect, the invention features, in general, a chromatography sample module including a flow-through member having an inlet and an outlet and chromatography media within the flow-through member. A sample is added to the media, and the module, with the sample carried therein, can then be connected to a separation column.

Preferably the chromatography sample module is a tubular member that is sized to fit within the end of a chromatography column that is used for separation of the sample contained on the media in the module. Alternatively, the module can be connected to the chromatography separation column by a flow line. The sample in the dissolution solvent can be added to the sample module, and then the dissolution solvent can be evaporated. Alternatively, the sample in the dissolution solvent can be added to the sample module as a liquid without evaporation.

In yet another alternative aspect the invention features a rack of sample modules arranged in an array.

Embodiments of these aspects invention may include one or more of the following advantages. The samples can be easily introduced into separation columns. Various solvents can be used for separation and dissolution of the sample, permitting optimization of the separation procedure. Samples are easily preprocessed, and the operator is not exposed to the media before or after adding the sample. A large number of samples can be prepared for processing at one time, facilitating the carrying out of multiple separations at one time.

Other features and advantages of the invention will be apparent from the following description of the preferred embodiments thereof and from the claims.

DESCRIPTION OF THE PREFERRED EMBODIMENTS

Figure 1:
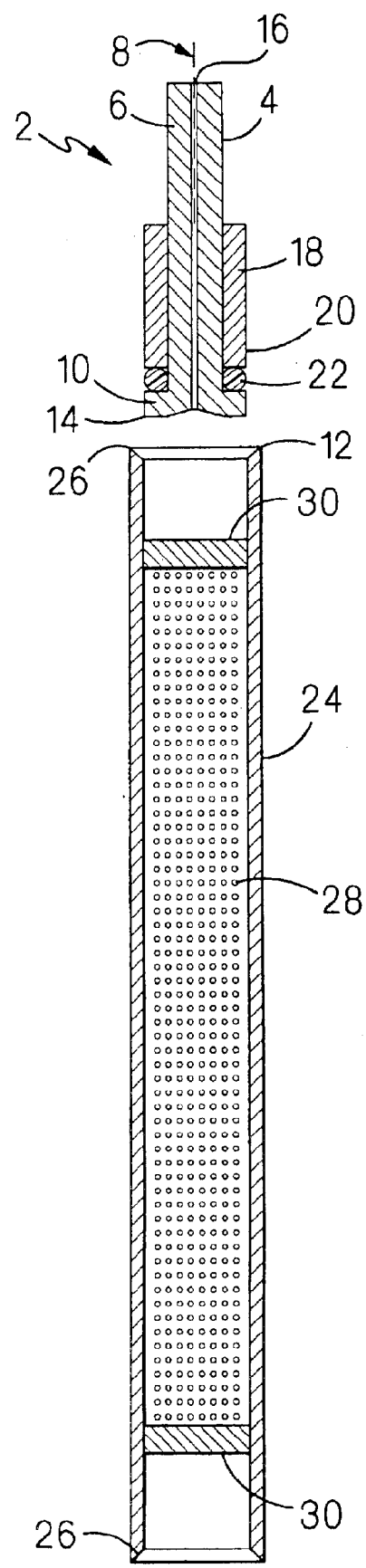
FIG. 1 is a diagrammatic cross-sectional view of a sealing apparatus according to the invention and a chromatography cartridge.
Figure 2:
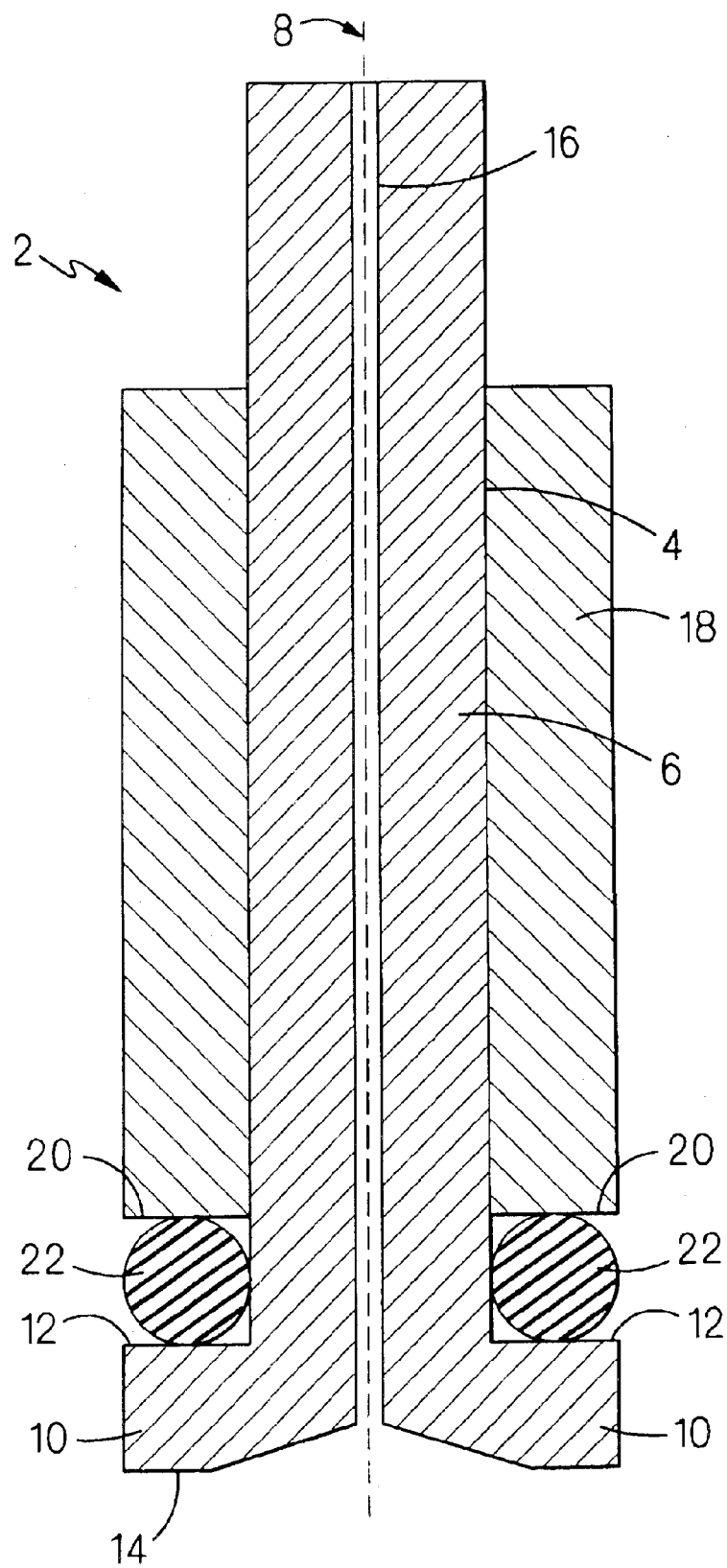
FIG. 2 is a diagrammatic cross-sectional view of a sealing apparatus according to the invention.
Figure 3:
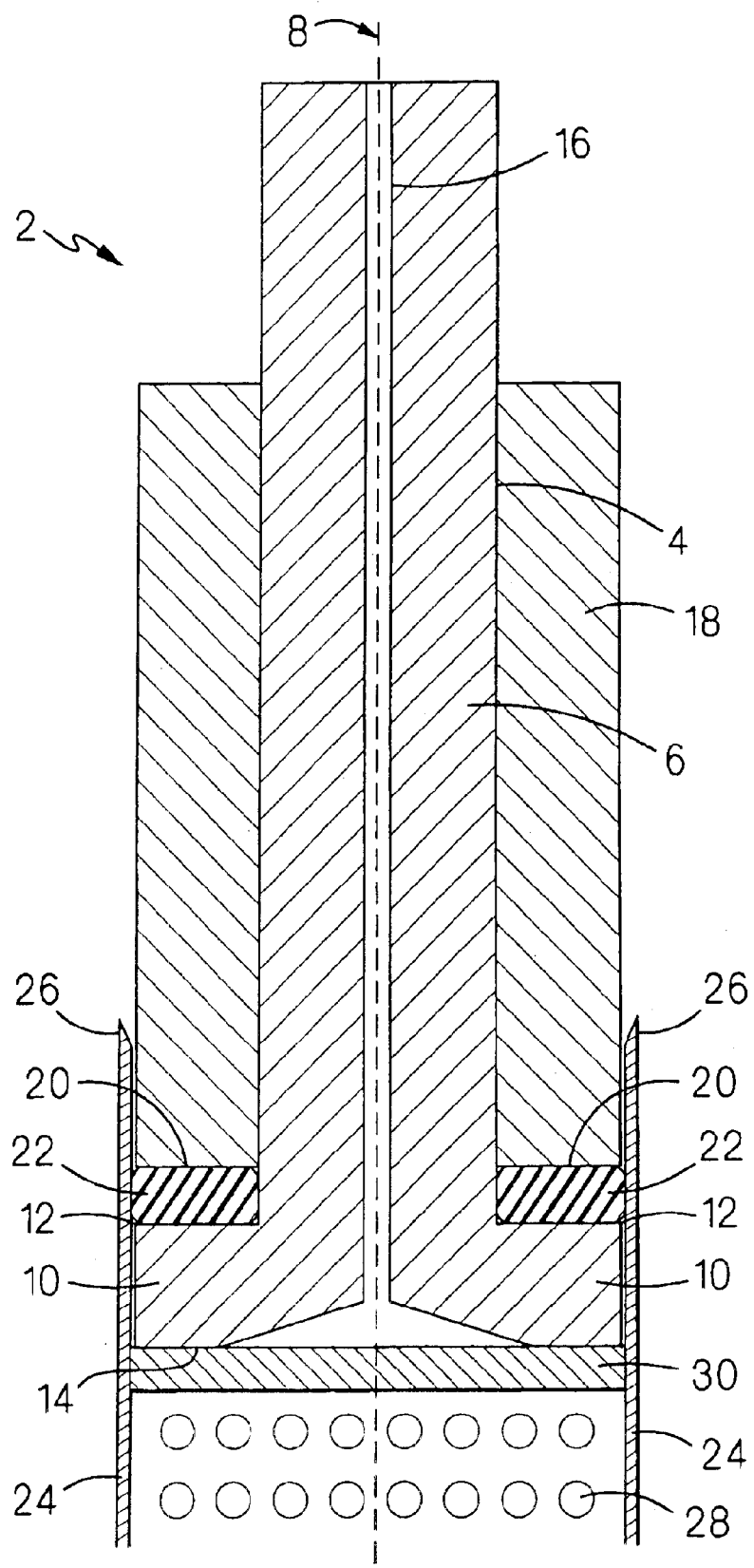
FIG. 3 is a diagrammatic cross-sectional view of a sealing apparatus according to the invention showing the formation of a seal with a chromatography cartridge.

Referring to FIGS. 1–3, there is shown a sealing apparatus employing sealing head 2, which includes first head piece 4, having body 6 with longitudinal axis 8. First head piece 4 has outwardly-extending shoulder 10, first compression face 12 that is located on shoulder 10, and contact face 14. Part of contact face 14 has a slightly conical shape or other concavity (exaggerated in FIGS. 2 and 3). First head piece 4 defines flow path 16 along axis 8. Second head piece 18, which includes second compression face 20 and a compression force receiving member extending thereabove, is sized to slidably receive body 6 of first head piece 4. Elastomeric sealing member 22 is at least partially situated between first compression face 12 and second compression face 20.

Sealing head 2 and its components are sized to fit slidably into cartridge 24, having chamfered edges 26, and chromatography media 28 bounded axially by porous plates 30 which form a rigid stop within the cartridge.

The connection of the apparatus is shown in FIGS. 1 and 3. As shown in FIG. 1, first head piece 4, elastomeric sealing member 22, and second head piece 18 are oriented so that they may slide into cartridge 24. As shown in FIG. 3, after first head piece 4, elastomeric sealing member 22, and second head piece 18 are situated within cartridge 24, and contact face 14 is stopped at porous plate 18, additional downward force on second head piece 18 causes first head piece 4 and second head piece 18 to be moved toward each other, thus axially compressing elastomeric sealing member 22 between first compression face 12 and second compression face 20. The axial compression of elastomeric sealing member 22 causes it to expand laterally and press against cartridge 24, thus forming a seal.

As shown in FIG. 3, insertion of sealing head 2 can create a close connection between contact face 14 and porous plate 30. Compressing elastomeric sealing member 22 between first compression face 12 and second compression face 20, by pressing second head piece 18 against elastomeric sealing member 22, which in turn presses first head piece 4 against porous plate 30, can maintain a close connection between contact face 14 and porous plate 30 while forming a seal between sealing head 2 and cartridge 24.

In the preferred combination, sealing head 2 is used to seal cartridge 24 having flexible walls. In other combinations, sealing head 2 is part of a containment structure assembly for receiving cartridge 24. The containment structure assembly may be pressurizable, such as a pressure vessel assembly that receives cartridge 24, compresses the flexible walls of cartridge 24, and provides uniform packing for chromatography media 28 therein. A containment structure of this type is discussed in U.S. Pat. No. 4,250,035 to McDonald, et al., which is incorporated herein by reference. Another type of pressurizable containment structure is discussed in U.S. Pat. No. 5,601,708 to Leavesley, which is also incorporated herein by reference. In other combinations, sealing head 2 is used to seal cartridge 24 having rigid walls.

The radial displacement of the outer surface of elastomeric sealing member 22 accommodates a range of inner diameters of cartridge 24, permitting effective seals while relaxing tolerances for the inner diameter of cartridge 24 to ±0.005".

Figure 4A:
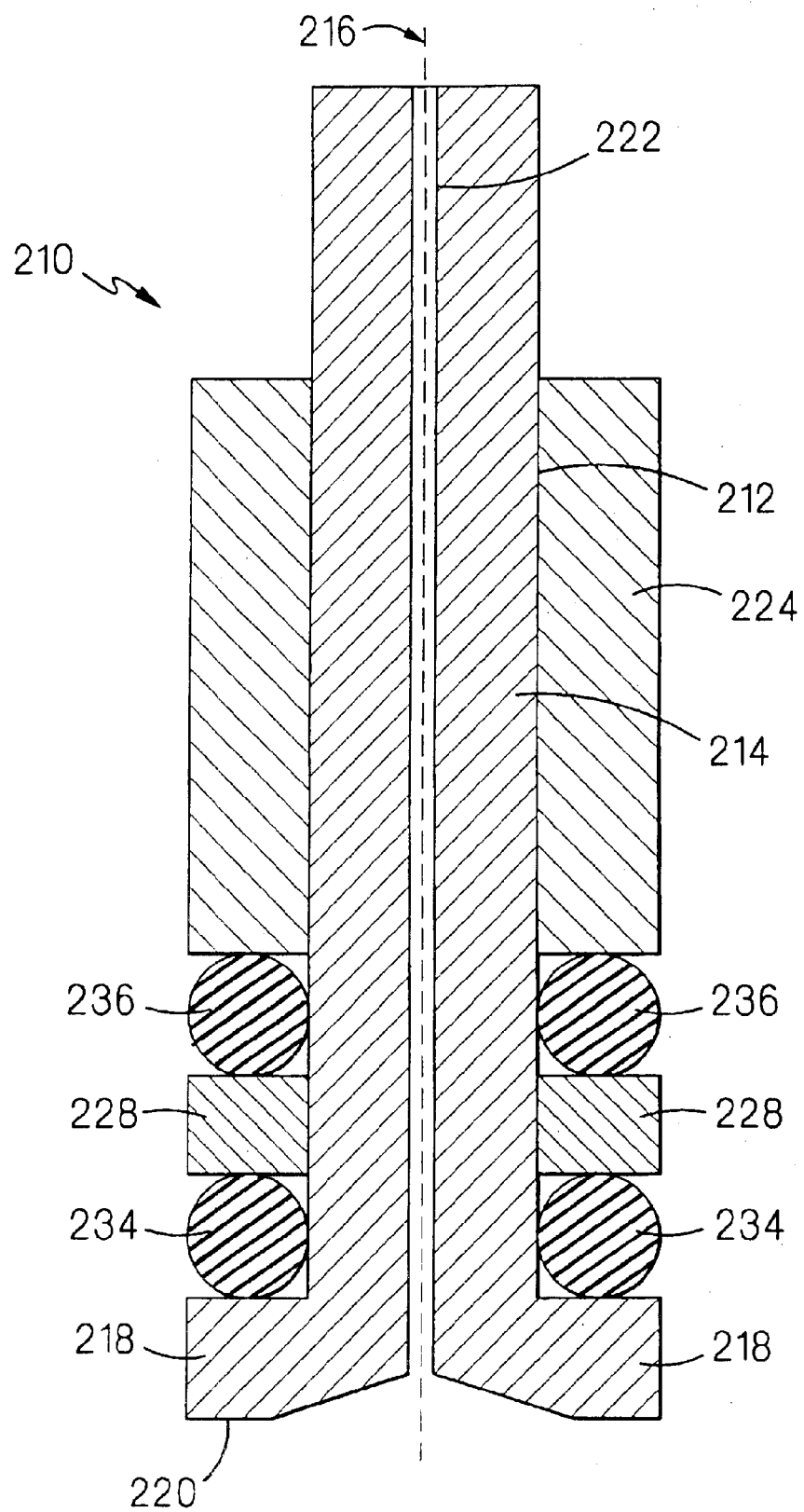
FIG. 4A is a diagrammatic vertical-sectional view of a sealing apparatus according to the invention.
Figure 4B:
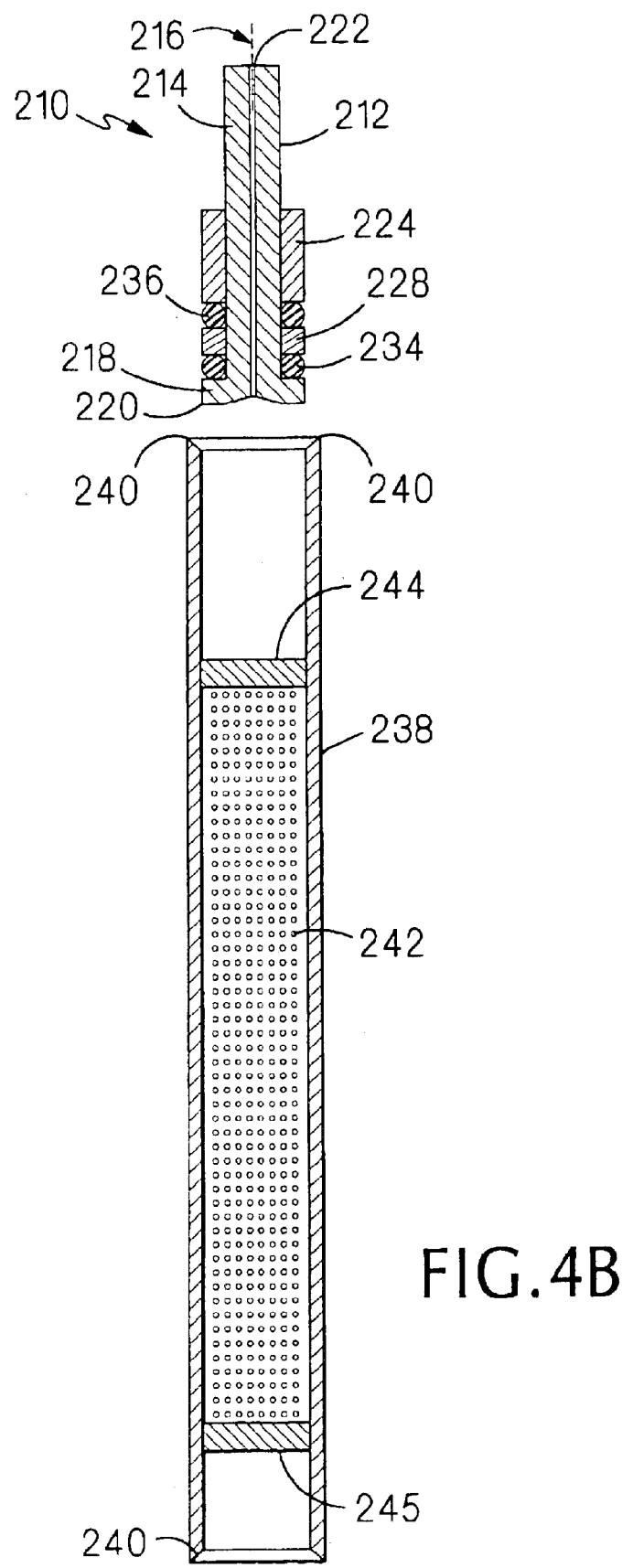
FIG. 4B is a diagrammatic vertical-sectional view of a sealing apparatus according to the invention and a chromatography column.
Figure 4C:
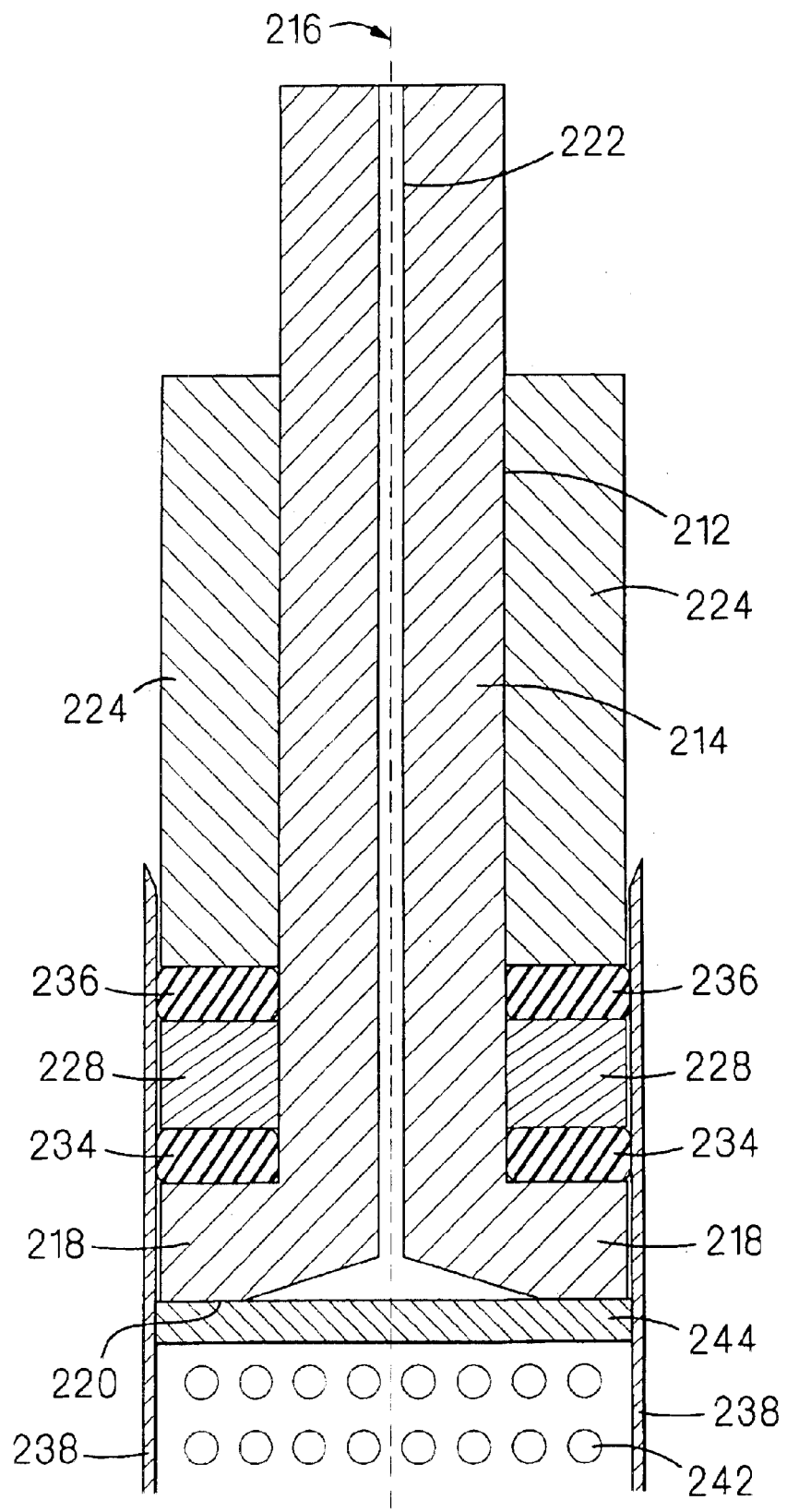
FIG. 4C is a diagrammatic vertical-sectional view of a sealing apparatus according to the invention showing the formation of seals with a chromatography column.

Referring to FIGS. 4A–4C, there is shown an alternate preferred embodiment of a sealing apparatus employing sealing head 210, which includes first head piece 212, second head piece 224, intermediate head piece 228, and first and second annular elastomeric sealing members 234, 236.

First head piece 212 has body 214 with longitudinal axis 216. First head piece 212 has outwardly extending shoulder 218, and contact face 220. Part of contact face 220 has a slightly conical shape or other concavity. First head piece 212 defines flow path 222 along axis 216.

Body 214 of first head piece 212 fits slidably through second head piece 224, intermediate head piece 228, and through first and second elastomeric sealing members 234, 236.

First elastomeric sealing member 234 is adjacent to both shoulder 218 and intermediate head piece 228. Second elastomeric sealing member 236 is adjacent to both intermediate head piece 228 and second head piece 224.

Sealing head 210 and its components are sized to fit slidably into column 238, having chamfered edges 240, filled with chromatography media bed 242, which is bounded axially by porous plates 244, 245.

The connection of the apparatus is shown in FIGS. 4B and 4C. As shown in FIG. 4B, first head piece 212, second head piece 224, intermediate head piece 228, and elastomeric sealing members 234, 236 are oriented so that they may slide into column 238. As shown in FIG. 4C, after sealing head 210 is situated within column 224, first head piece 212 and second head piece 224 are moved relative to each other. This relative movement axially compresses first elastomeric sealing member 234 between shoulder 218 and intermediate head piece 228 and also compresses second elastomeric sealing member 236 between intermediate head piece 228 and second head piece 224. The axial compression of elastomeric sealing members 234, 236 causes them to expand laterally and press against the interior surface of column 238, thus forming seals.

As shown in FIG. 4C, insertion of sealing head 210 can create a close connection between contact face 220 and porous plate 244. Compressing elastomeric sealing members 234, 236, by pressing second head piece 224 against second elastomeric sealing member 236, which in turn presses second elastomeric sealing member 236 against intermediate head piece 228, intermediate head piece 228 against first elastomeric sealing member 234, first elastomeric sealing member against shoulder 218, and contact face 220 against porous plate 244, can maintain a close connection between contact face 220 and porous plate 244 while forming a seal between sealing head 210 and column 238.

Figure 6:
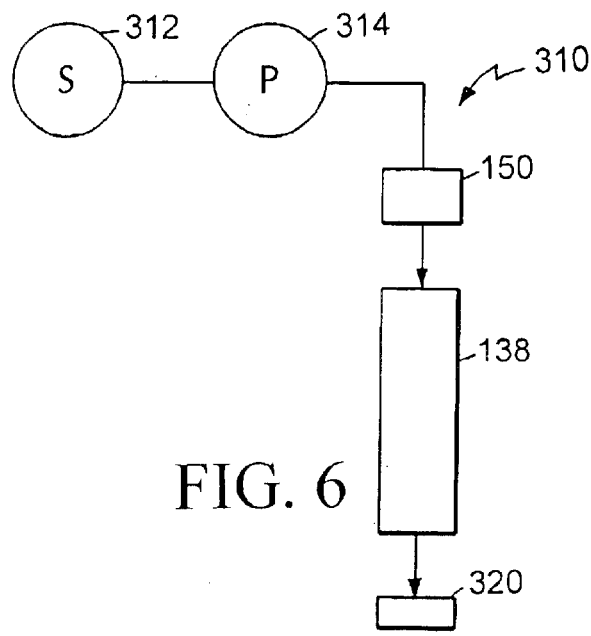
FIG. 6 is a schematic diagram of a chromatography system according to the invention.
Figure 7:
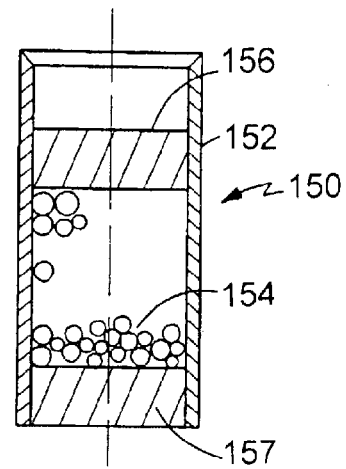
FIG. 7 is a vertical sectional view of a chromatography sample module used in the FIG. 6 system.

Referring to FIG. 6, there is shown chromatography system 310 which includes a source of solvent 312, pump 314, sample module 150, liquid chromatography column 138, and sample collection vessel 320. In this system, the sample to be analyzed is preabsorbed onto media in sample module 150 prior to pumping solvent into module 150 and into chromatography column 138 to perform the separation procedure.

Referring to FIG. 2, it is seen that sample module 150 includes cylindrical plastic tube 152, porous plates 156, 157 (made of inert plastic porous frits), and chromatography media 154 (only partially shown in the figures) between porous plates 156, 157.

Figure 5A:
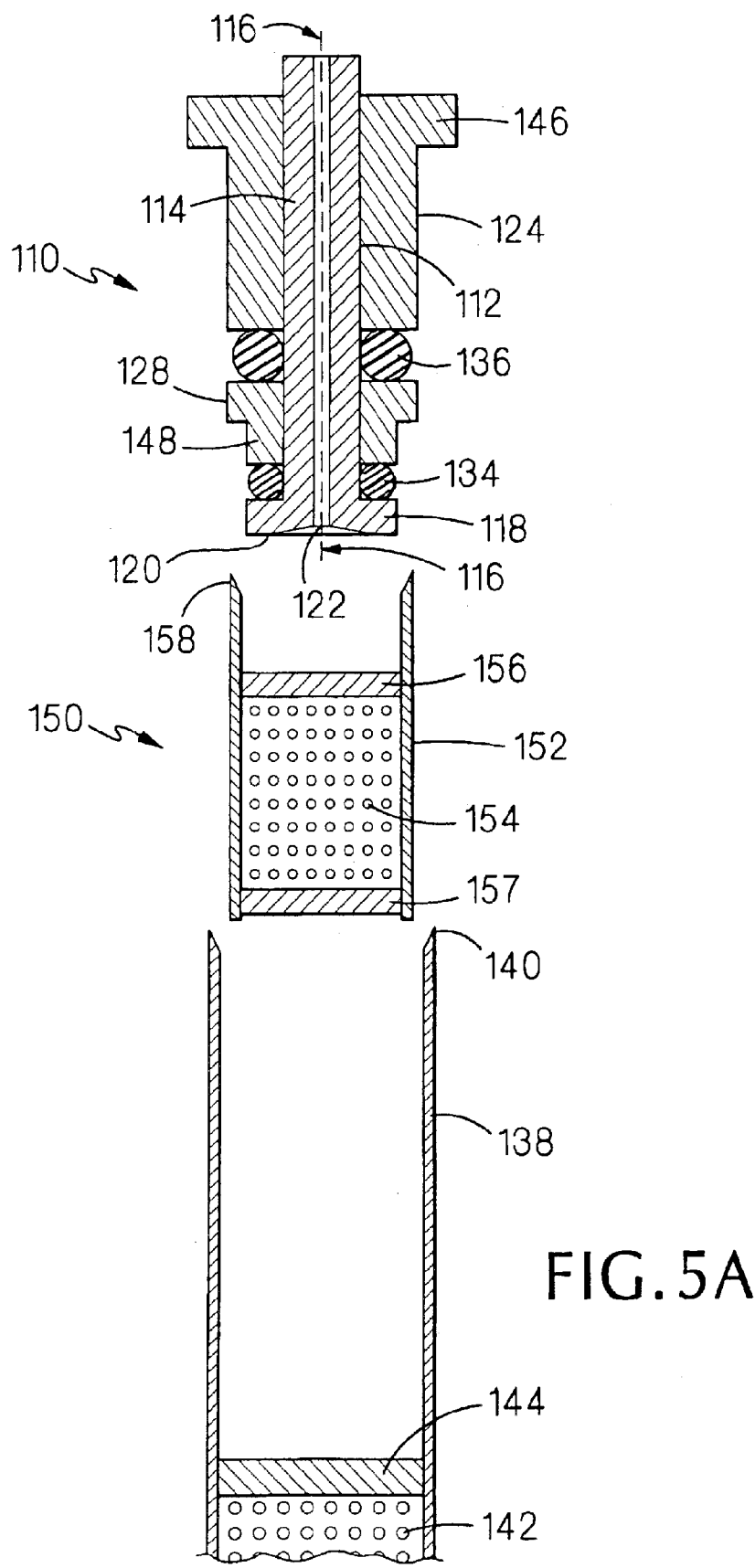
FIG. 5A is a diagrammatic exploded vertical-sectional view of an alternate sealing apparatus according to the invention with a chromatography column.
Figure 5B:
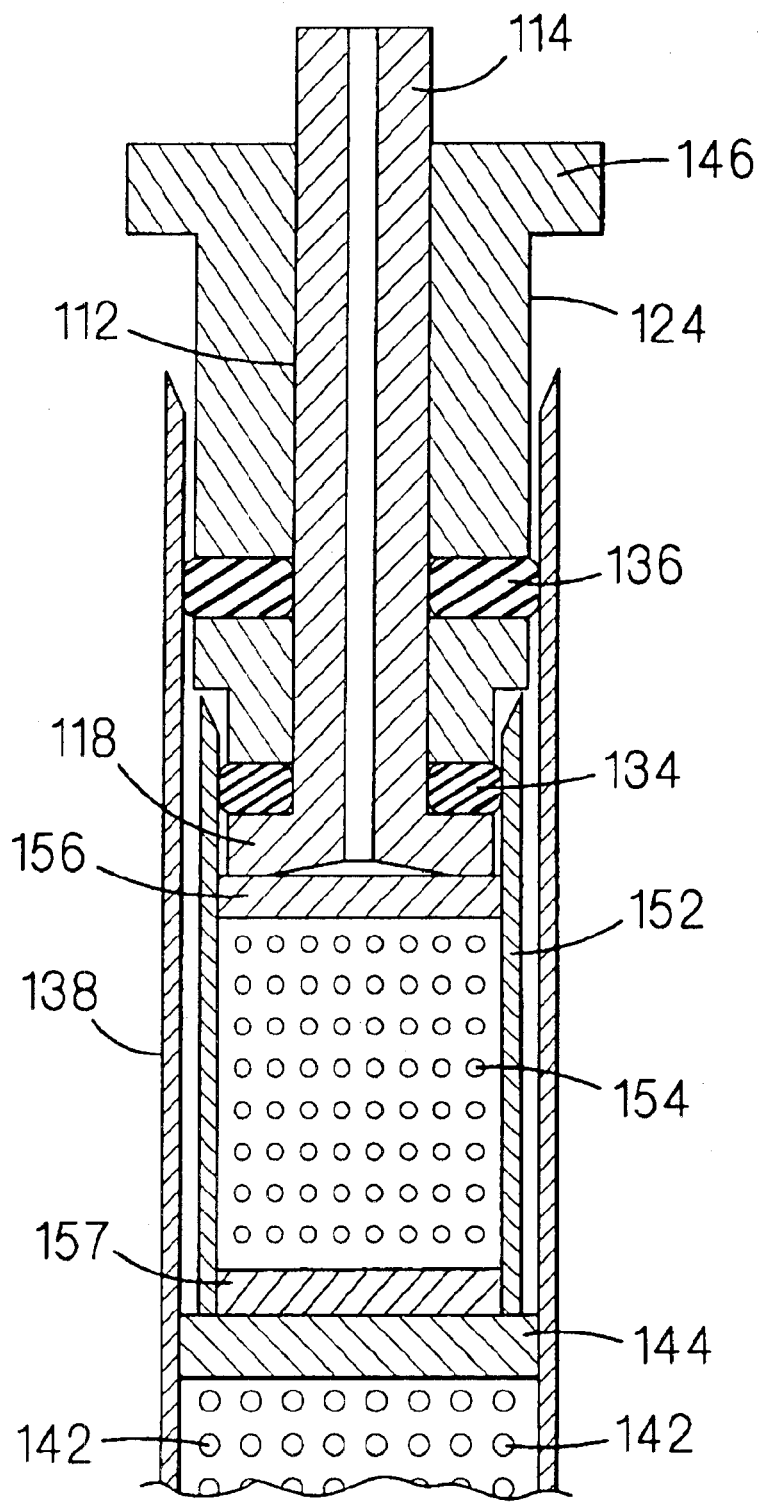
FIG. 5B is a diagrammatic vertical-sectional view of an alternate sealing apparatus according to the invention showing the formation of a seal with a chromatography column.

As appears from FIGS. 5A and 5B, sample module 150 is designed to fit within chromatography column 138 at the entrance thereof and to be sealably connected to the sealing head. Tube 152 is designed to fit within column 138 with minimal space between the two; in particular, there is 0.000" to 0.010" of radial clearance.

Sample module 150 can be filled with media that is the same as or is different from the media of chromatography column 138. The sample is dissolved in the required solvent and added to the top of sample module 150, where it is drawn into the media by capillary action. This dissolution solvent is then removed by placing sample module 150 in a vacuum chamber. Heat may also be applied.

After sample module 150 has dried, it can be placed directly inside separation column 138 so that the lower porous plate 157 is an in intimate contact with the surface of the separation media or with a porous plate within the separation column on top of the separation media.

Alternatively, sample module 150 can be placed in a remote tube connected by a solvent line. Alternatively, the sample can be dissolved in a separation solvent (or a weaker solvent), and added to module 150. The wet module can then be loaded into the column or into a remote tube.

Examples of the types of complex samples where this technique has particularly advantageous use include synthetic organic reaction mixtures and natural product extracts, (e.g., from fermentation broths or plants). These samples often need to be dissolved in a solvent not compatible with the optimized separation solvent. Solvents are organized according to their "solvent strength," where hexanes have a value close to zero, and methanol has a value of 0.95. Optimized separation eluents often have a lower solvent strength; e.g., hexane:ethylacetate 1:1 has a solvent strength of 0.295. If the sample needs to be dissolved in a strong solvent such as methanol, there will be a solvent strength difference of 0.655 seen initially after loading the sample onto the column, and this will impair the separation of the sample. If the sample dissolved in methanol is instead preadsorbed to the media in the sample module and dried, the sample will not face this impairment during separation.

Figure 8:
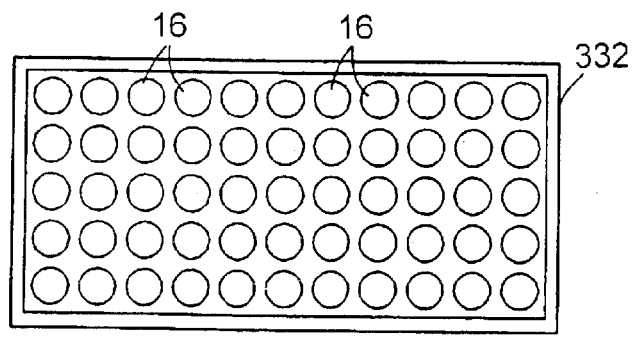
FIG. 8 is a plan view of a rack containing a plurality of the FIG. 7 sample modules in an array.
Figure 9:
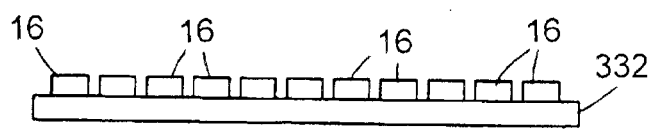
FIG. 9 is an elevation of the FIG. 8 rack and modules.

Referring to FIGS. 8 and 9, sample modules 150 can be supplied in racks 332, and a whole rack of sample modules 150 can be efficiently prepared at one time rather than one at a time.

FIGS. 5A and 5B show the placement of a module 150 in a column 138 and the sealing of the module 150 and column 138 to a sealing head used to deliver solvent. Sealing head 110 has first head piece 112, second head piece 124, intermediate head piece 128, and first and second annular elastomeric sealing members 134, 136.

First head piece 112 has body 114 with longitudinal axis 116. First head piece 112 has outwardly extending shoulder 118, and contact face 120. Part of contact face 120 has a slightly conical shape or other concavity. First head piece 112 defines flow path 122 along axis 116.

Body 114 of first head piece 112 fits slidably through central openings in second head piece 124, intermediate head piece 128, and first and second elastomeric sealing members 134, 136.

Second head piece 124 has outwardly extending compression force receiving member 146. Intermediate head piece 128 has narrow portion 148 distal from second head piece 124.

First elastomeric sealing member 134 is adjacent to both shoulder 118 and narrow portion 148 of intermediate head piece 128. Second elastomeric sealing member 36 is adjacent to both intermediate head piece 128 and second head piece 124.

Sample module 150 has tube 152 which contains second chromatography media bed 154 bounded axially by second porous plates 156, 157. The outer diameter of tube 152 is sized so that sample module 150 fits into column 138. The inner diameter of tube 152 is sized so that it may slidably receive shoulder 118, first elastomeric sealing member 134, and narrow portion 148 of intermediate head piece 128.

Intermediate head piece 128, second elastomeric sealing member 136, and second head piece 124 are sized to fit slidably into column 138, having chamfered edges 140, filled with first chromatography media bed 142, which is bounded axially by first porous plates 144.

Referring to FIG. 5B seals are formed with the apparatus by inserting sample module 150 into column 138 so that second porous plate 157 abuts first porous plate 144. Sealing head 110 is then inserted into column 138 and tube 152 of sample module 150, so that shoulder 118, first elastomeric sealing member 134, and narrow portion 148 are within tube 152, and contact face 120 abuts second porous plate 156. Sealing head 110 extends far enough into column 138 so that second elastomeric sealing member 136 opposes the inner surface of column 138.

Downward compressive force applied to outwardly extending compression force receiving member 146 causes second head piece 124 to slide relative to first head piece 112 and transmits compressive force to second elastomeric sealing member 136, intermediate head piece 128, first elastomeric sealing member 134, shoulder 118, second porous plate 156, first media bed 154, second porous plate 157, first porous plate 144, and first media bed 142. The compressive force causes first and second elastomeric sealing members 134, 136 to expand radially so that first elastomeric sealing member 134 forms a seal with tube 152 and second elastomeric sealing member 136 forms a seal with column 138.

The seals are released by applying an upward force to second head piece 124, thereby reducing the compressive force on the components of sealing head 110 and reducing the radial expansion of elastomeric sealing members 134, 136.

Preferably, cartridge 24 and tube 152 are made of high-density polyethylene. However, columns and cartridges may be constructed of other materials, including glass or stainless steel. Preferably, elastomeric sealing member 22 is made of a fluorocarbon polymer, such as that sold under the trade name CHEMRAZ.

What is claimed is:

1. A chromatography column comprising:
   a tubular member having an inlet end, an outlet end, an inner surface, and a longitudinal axis;
   first and second porous members disposed within said tubular member; and
   a chromatography media disposed within said tubular member, said chromatography media being bounded axially between said first and second porous members;
   wherein said first porous member is spaced sufficiently from said inlet end to define an inflow region, within said tubular member and between said first porous member and said inlet end, and said second porous member is spaced sufficiently from said outlet end to define an outflow region, within said tubular member and between said second porous member and said outlet end, said inflow region being substantially longer than said outflow region.

2. The chromatography column of claim 1 wherein said inner surface is sufficiently smooth, near said first porous member, so as to render said first porous member moveable relative to said tube, when subject to compressive force, so that said first porous member can compress said media.

3. The chromatography column of claim 2 wherein said inner surface is sufficiently smooth, near said second porous member, so as to render said second porous member moveable relative to said tube, when subject to compressive force, so that said second porous member can compress said media.

4. The chromatography column of claim 1 wherein said inner surface is sufficiently smooth, near said second porous member, so as to render said second porous member moveable relative to said tube, when subject to compressive force, so that said second porous member can compress said media.

5. The chromatography column of claim 1 wherein said inflow region comprises a module receiving region between said first porous member and said inlet end, said module receiving region being sufficiently long to receive a sample module entirely within said inflow region.

6. The chromatography column of claim 5 wherein said inflow region further comprises a sealing region between said module receiving region and said inlet end, said sealing region being sufficiently long to receive a sealing head for making a seal with said inner surface of said tubular member.

7. The chromatography column of claim 1 wherein said outflow region is sized to receive a sealing head for making a seal with said inner surface of said tubular member.

8. The chromatography column of claim 1 wherein said inner surface of said tubular member is substantially cylindrical.

9. The chromatography column of claim 1 wherein said inner surface of said tubular member is substantially cylindrical throughout said inflow region.

10. The chromatography column of claim 1 wherein said inner surface of said tubular member is substantially cylindrical throughout said outflow region.

11. The chromatography column of claim 1 wherein said tubular member further comprises a first chamfered region near said inlet end.

12. The chromatography column of claim 11 wherein said tubular member further comprises a second chamfered region near said outlet end.

13. The chromatography column of claim 1 wherein said tubular member further comprises a second chamfered region near said outlet end.

14. The chromatography column of claim 5, further comprising a tubular sample module disposed within said module receiving region, a second media within said sample module, and a chromatography sample carried on said second media, said sample module having a module inner surface, a module inlet end and a module outlet end.

15. The chromatography column of claim 14 wherein said chromatography sample had been added to said media by:
    providing said second media prepacked within said sample module;
    dissolving said sample in a solvent;
    adding said solvent and said dissolved sample to said prepacked media; and evaporating said solvent.

16. The chromatography column of claim 14 wherein said chromatography sample module further comprises a module sealing region, between said second media and said module inlet end, said module sealing region being sufficiently long to receive a module sealing head for making a seal with said module inner surface.

17. The chromatography column of claim 16 further comprising a first sealing head having a first elastomeric sealing member for making a seal with said inner surface at said sealing region.

18. The chromatography column of claim 17 wherein said first sealing head further comprises a second elastomeric sealing member for making a seal with said module inner surface.

19. The chromatography column of claim 17 further comprising a second sealing head having a third elastomeric sealing member for making a seal with said inner surface at said outflow region.

20. The chromatography column of claim 1 wherein said tubular member is made of a flexible material capable of radial compression.

21. A chromatography column comprising:
    a tubular member having an inlet end, an outlet end, an inner surface, and a longitudinal axis;
    first and second porous members disposed within said tubular member; and
    a chromatography media disposed within said tubular member, said chromatography media being bounded axially between said first and second porous members;
    wherein said first porous member is spaced sufficiently from said inlet end to define an inflow region, within said tubular member and between said first porous member and said inlet end, and said second porous member is spaced sufficiently from said outlet end to define an outflow region, within said tubular member and between said second porous member and said outflow end, said inner surface being substantially cylindrical at said inflow region, said inner surface being sufficiently smooth, near said first porous member, so as to render said first porous member moveable relative to said tube, under compressive force, so that said first porous member can compress said media.

22. The chromatography column of claim 21 wherein said inner surface is sufficiently smooth, near said second porous member, so as to render said second porous member moveable relative to said tube, under compressive force, so that said second porous member can compress said media.

23. The chromatography column of claim 21 wherein said inflow region is sized to receive a sealing head for making a seal with said inner surface of said tubular member.

24. The chromatography column of claim 21 wherein said outflow region is sized to receive a sealing head for making a seal with said inner surface of said tubular member.

25. The chromatography column of claim 21 wherein said inner surface of said tubular member is substantially cylindrical.

26. The chromatography column of claim 21 wherein said inner surface of said tubular member is substantially cylindrical throughout said inflow region.

27. The chromatography column of claim 21 wherein said inner surface of said tubular member is substantially cylindrical throughout said outflow region.

28. The chromatography column of claim 21 wherein said tubular member further comprises a first chamfered region near said inlet end.

29. The chromatography column of claim 28 wherein said tubular member further comprises a second chamfered region near said outlet end.

30. The chromatography column of claim 21 wherein said tubular member is made of a flexible material capable of radial compression.

31. The chromatography column of claim 21 further comprising a first sealing head having a first elastomeric sealing member for making a seal with said inner surface at said sealing region.

32. The chromatography column of claim 31 wherein said first sealing head further comprises a second elastomeric sealing member for making a seal with said inner surface at said sealing region.

33. The chromatography column of claim 31 further comprising a second sealing head having a third elastomeric sealing member for making a seal with said inner surface at said outflow region.

34. A chromatography column comprising:
a tubular member having an inlet end, an outlet end, an inner surface, and a longitudinal axis;
first and second porous members disposed within said tubular member; and
a chromatography media disposed within said tubular member, said chromatography media being bounded axially between said first and second porous members;
wherein said first porous member is spaced sufficiently from said inlet end to define an inflow region, within said tubular member and between said first porous member and said inlet end, and said second porous member is spaced sufficiently from said outlet end to define an outflow region, within said tubular member and between said second porous member and said outflow end, said inner surface being substantially cylindrical at said inflow region, said inner surface being sufficiently smooth, near said first porous member, so as to render said first porous member moveable relative to said tube, under compressive force, so that said first porous member can compress said media, said inflow region being substantially longer than said outflow region.

* * * * *